United States Patent [19]

Dau

[11] 4,201,092
[45] May 6, 1980

[54] METHOD OF DETECTING AND MONITORING A LEAK CAUSED BY A THROUGH WALL CRACK IN A HIGH PRESSURE FLUID SYSTEM

[75] Inventor: Gary J. Dau, Palo Alto, Calif.

[73] Assignee: Electric Power Research Institute, Inc., Washington, D.C.

[21] Appl. No.: 830,988

[22] Filed: Sep. 6, 1977

[51] Int. Cl.$^2$ .................. G21C 17/00; G01N 9/24
[52] U.S. Cl. ............................. 73/587; 176/19 LD
[58] Field of Search ................ 176/19; 73/587, 659

[56] References Cited

U.S. PATENT DOCUMENTS 3,545,262  12/1970  Steele et al. .................. 176/19 R

FOREIGN PATENT DOCUMENTS 2253219  6/1975  France .......................... 176/19 R

OTHER PUBLICATIONS

Trans Actions of 3rd International Conference on Structural Mechanics in Reactor Technology, vol. 3, part G London, 9/1–5/76, G 3/9 pp. 1–16 Sinclair et al. G 3/8 pp. 1–14 Ingham et al.
G 3/7 pp. 1–14 Ingham et al. (II).
Machine Design, vol. 45 (6/14/73) pp. 132–137 Herzog.
S3045 0056 (5/9–11/72) Schofield pp. 76–82.
Technical Report DRC-71-2 (5/71) Harris et al. pp. 1–14.
ANS Transactions, 11/14–19/76 pp. 393–397.

Primary Examiner—Samuel W. Engle
Assistant Examiner—S. A. Cangialosi
Attorney, Agent, or Firm—Flehr, Hohbach, Test, Albritton & Herbert

[57] ABSTRACT

A method of detecting and monitoring leaks in the piping of a nuclear reactor senses the acoustic energy from the leak and analyzes its frequency spectrum versus acoustic amplitude. A choke flow condition will exist where the leak flows at sonic velocity; here the acoustic energy is directly proportional to the area of the crack producing the leak. This is utilized to provide an indication of crack enlargement.

1 Claim, 5 Drawing Figures

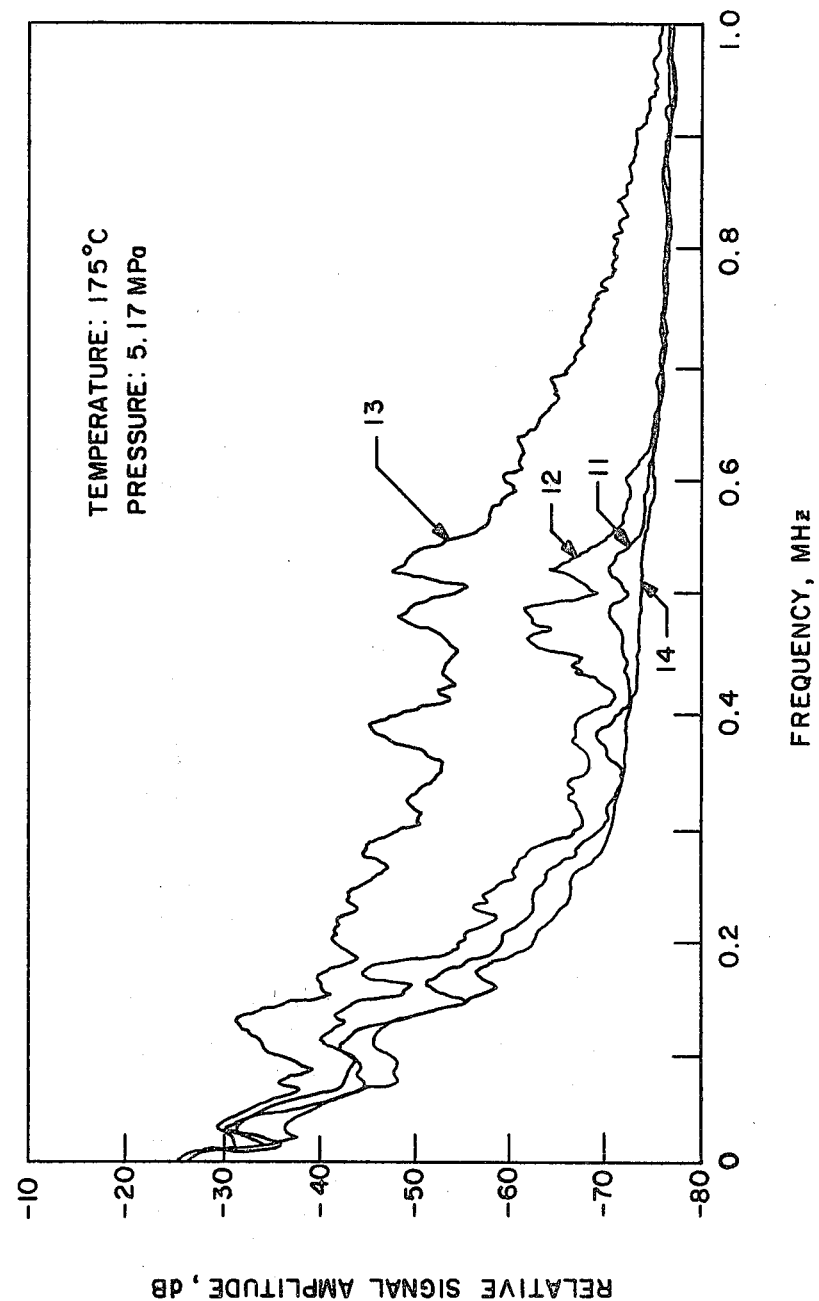

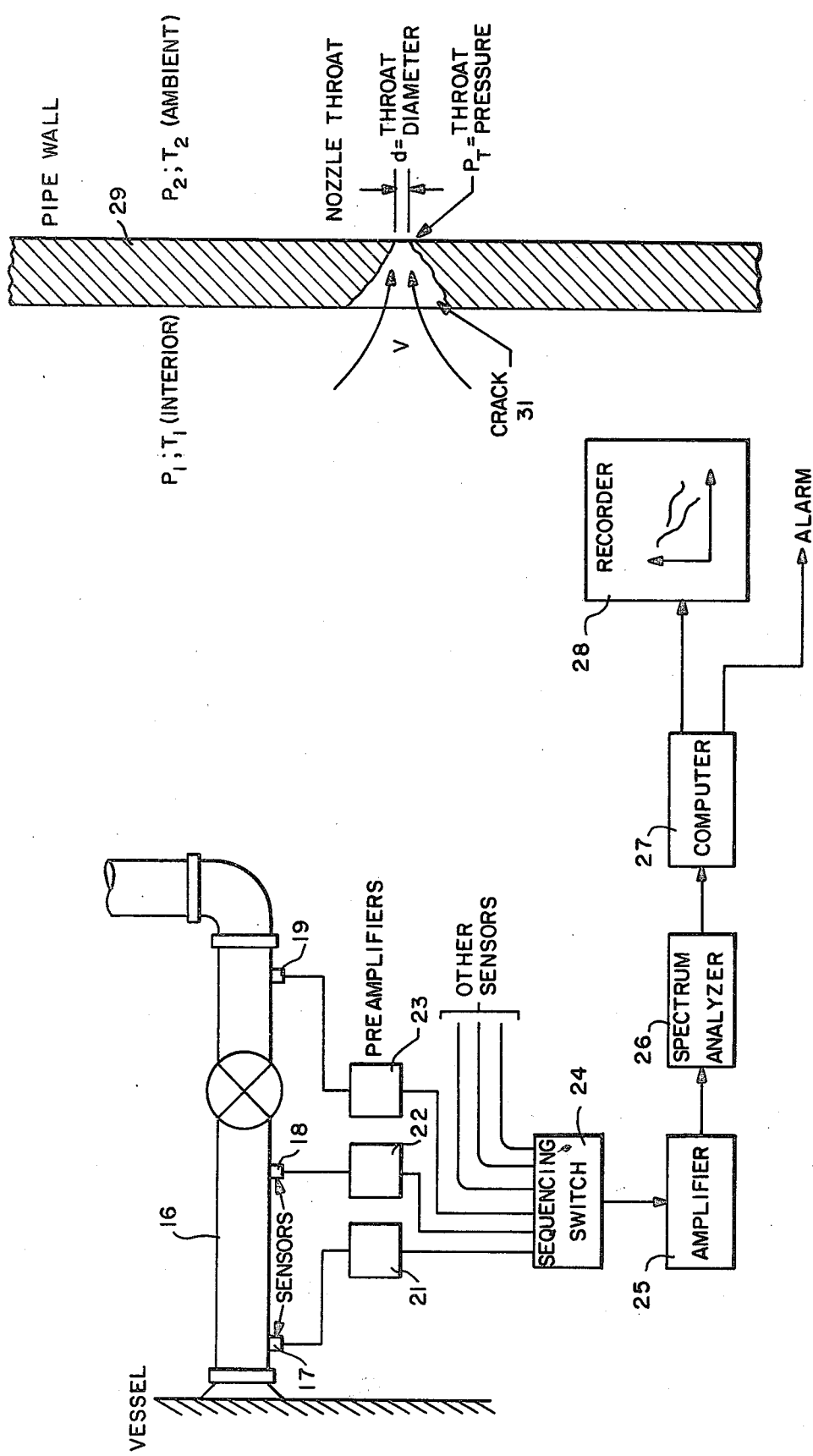

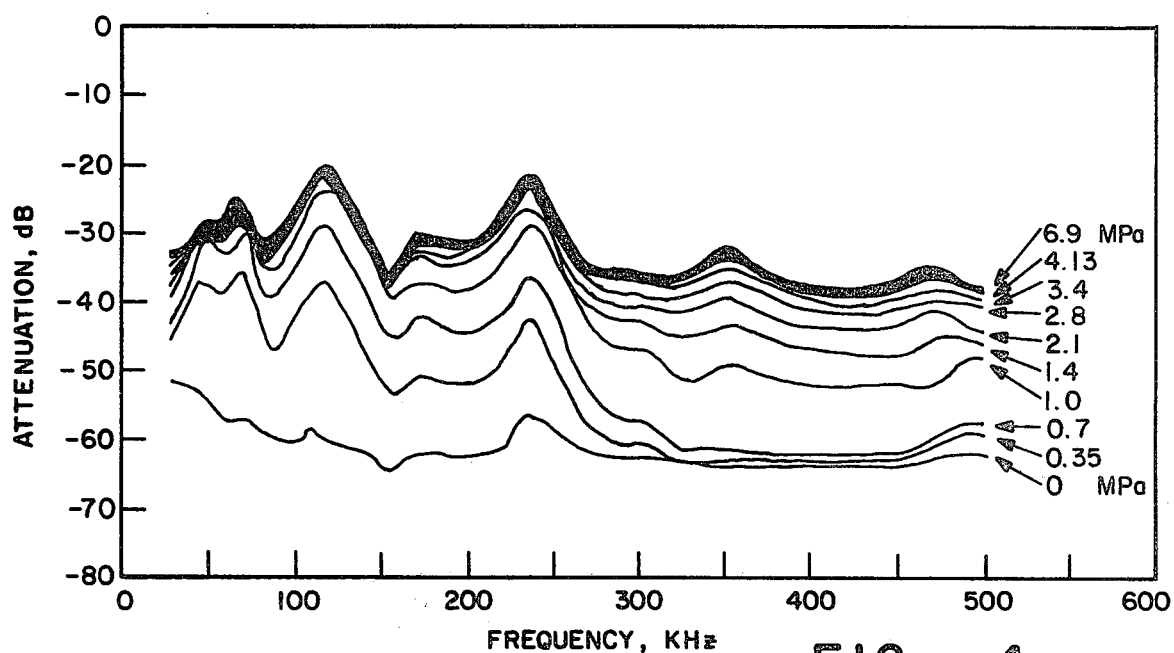
FIG.—4
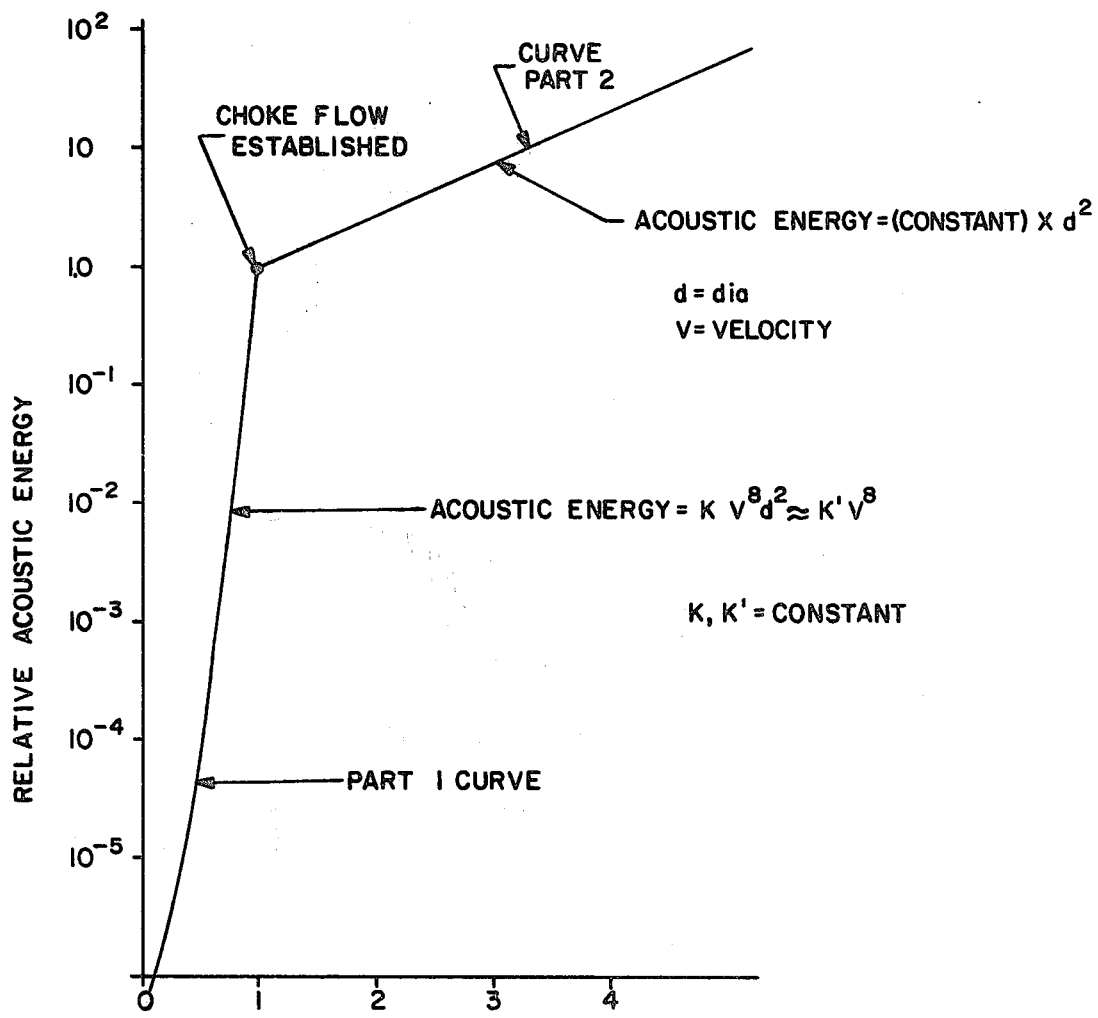
FIG.—5

METHOD OF DETECTING AND MONITORING A LEAK CAUSED BY A THROUGH WALL CRACK IN A HIGH PRESSURE FLUID SYSTEM

BACKGROUND OF THE INVENTION

The present invention is directed to a method of detecting and monitoring a leak caused by a through wall crack in a high pressure fluid system and more specifically to a nuclear reactor piping system.

Nuclear piping systems are designed under code provisions that reflect a leak-before-break philosophy. Piping is typically austenitic stainless steel and past service history has shown that through wall cracks will occur without serious threat to system integrity; i.e., the pipe breaking. Thus, leak detection is an important method for detecting a fracture process in these piping systems.

In reactor systems where large volumes and flow rates are involved it is believed that detection of escaping fluids holds the most promise for improved sensitivity. Several present techniques now in use on reactor systems include flow detection, radio isotope gas detection, nuclear radiation detection, and pressure and temperature changes in a "collection" chamber. Methods which have been proposed for future use include acoustic noise monitoring and moisture sensitive foil which exhibits a conductivity change in the presence of moisture.

One form of acoustic monitoring which has been developed is acoustic emission. Usually acoustic emission is defined as the elastic waves generated when a material undergoes plastic deformation. Here when the structure is loaded, emissions occur in burst type pulses and it is possible to calculate source location with the use of several transducers which are affixed directly to the structure being monitored.

A definitive study in the application of acoustic emission to leak detection was made to J. D. Allison, O. A. Kupcis, and O. C. Irwin, "Detection of Leaks in CANDU Reactor Fuel Channels Using Acoustic Emission Monitoring," CWAPD-267 Westinghouse Canada Limited, Dec. 5, 1974. Here a transducer was in contact with the end fitting of each of the several pressure tubes in the reactor. Frequency analysis of the detected signal was conducted in the frequency range up to 1.0 MHz. As illustrated in FIG. 1, signals were analyzed on a frequency amplitude basis and the frequency spectra for the tubes indicated as 11, 12 and 13 were identified as leaking tubes as opposed to the nonflawed or sound tube represented by curve 14. In other words, this experiment indicated that by the use of acoustic emission in a frequency amplitude plot, the presence of a leak might be indicated by the frequency distribution or frequency spectra.

However, merely detecting a leak is not sufficient. It is desired to quantify the leak and provide an indication of the crack growth through the wall of the piping. This would be a significant aid in determining operating and shutdown repair criteria.

OBJECTS AND SUMMARY OF THE INVENTION

It is, therefore, a general object of the present invention to provide an improved method of detecting and monitoring a leak caused by a through wall crack in a high pressure fluid system.

In accordance with the above object there is provided a method of detecting and monitoring a leak caused by a through wall crack in a high pressure fluid system. The acoustic energy emitted by the wall crack is sensed. Change of the sensed energy is monitored over time. Crack enlargement in accordance with the change of the sensed energy is determined.

BRIEF DESCRIPTION OF THE DRAWINGS

FIG. 1 is a set of curves illustrating prior art acoustic emission leak detection;

FIG. 2 is a schematic representation of an acoustic emission leak detection system embodying the present invention;

FIG. 3 is a cross-sectional view illustrating a through wall crack in the piping of FIG. 2 which is useful in understanding the invention;

FIG. 4 are frequency spectrum curves useful in understanding the invention; and

FIG. 5 is a curve illustrating the method of the present invention.

DETAILED DESCRIPTION OF THE PREFERRED EMBODIMENT

In the "Background of the Invention" the curves of FIG. 1 have already been explained as being obtained from several different high pressure pipes in a specific reactor where ultrasonic sensors were used to provide the signals which were later analyzed in the form as shown. FIG. 2 illustrates a system which could be used to generate the curves of FIG. 1 but which may also be adapted in conjunction with the method of the present invention.

Referring to FIG. 2, a single pipe 16 is illustrated with several ultrasonic transducers or sensors 17, 18, 19 mounted thereon at space locations. Each transducer includes a preamplifier 21, 22, 23 respectively whose outputs are time sequenced by a sequencing switch 24, amplified by amplifier unit 25 and connected to a spectrum analyzer 26. Such analyzer in combination with the computer 27 may make a Fourier analysis of a signal from a single sensor and displayed it on an XY plot recorder 28 where amplitude is the vertical axis and frequency the horizontal axis. Such is the case with the curve of FIG. 1. Here the presence of leaks in the pipes corresponding to curves 11, 12 and 13 is indicated by the peaks at various frequencies (which approach 1 MHz) as compared to the nonleaking or sound tube or pipe corresponding to the curve 14.

However, as stated above, merely sensing the presence of a leak is not sufficient. Enlargement or growth rate of a through wall crack is very desirable information. In accordance with the present invention it has been discovered that there is a physical similarity between a through wall crack and a nozzle. FIG. 3 illustrates a pipe wall 29 which, for example, might be a portion of pipe 16 of FIG. 2 where in the interior of the pipe there is a relatively high pressure $P_1$ and temperature $T_1$ and the ambient conditions on the outside are $P_2$; $T_2$. The crack is indicated at 31 where the external throat diameter is d, pressure at that point is $P_T$ and the velocity of the leaking fluid is indicated as V. When turbulent flow conditions exist in the crack, considerable acoustic energy is generated. From a general standpoint the following expression relates acoustic energy to flow conditions.

$$\text{Acoustic Energy} = K\rho_o V^8 A_o^{-5} d^2 \qquad (1)$$

$\rho_o$ = Density
V = Velocity
$A_o$ = Speed of sound in fluid
d = Diameter
K = Constant with typical value of $0.6 \times 10^4$ for Mach number between 0.3 and 1.0.

Such equation was propounded by M. J. Lighthill "On Sound Generated Aerodynamically" *Proceedings of the Royal Society* (London) A, 211 (1952), page 564, and 222 (1954), page 1. The terms of the equation can be related to the throat diameter of the nozzle and the velocity of the fluid. The maximum velocity obtainable for the nozzle is the speed of sound of the fluid, $A_0$. This occurs when the pressure at the throat reaches the critical pressure, $P_c$, and is where "choke flow" exists. Fluid velocity will remain constant at the sonic velocity as long as the critical pressure $P_c$ is equal to or greater than the ambient discharge pressure $P_2$. Moreover, with steam as a fluid it has been found that the ratio of critical pressure $P_c$ to the pressure $P_1$ is in the range of from 0.56 to 0.575.

When choke flow conditions persist, equation (1) reduces to the following expression:

$$\text{Acoustic Energy} = k\rho_o A_o^3 d^2 \quad (2)$$
$$= \text{Constant} \times d^2$$

This expression indicates that the acoustic energy generated is independent of the driving pressure once choke flow conditions are established. FIG. 4 illustrates the foregoing. This shows the frequency spectrum results obtained when a mockup tube is pressurized in stages up to 6.9 MegaPascals (MPa) (1,000 psi) with a 0.034 cm diameter hole drilled through the wall. The heavy darkened curve at 6.9 MPa shows that saturation of sound intensity occurs because the escaping fluid velocity reaches sonic velocity and thus remains constant.

Equation (2) also demonstrates that the energy at the choke flow condition is related only to the cross sectional area of the crack; thus, the monitoring of the energy generated will provide indication of crack enlargement. Such crack enlargement is determined by the fact that acoustic energy is directly proportional to the cross sectional area of the crack, i.e., $d^2$.

The relationship of equations (1) and (2) is better illustrated in FIG. 5 which is a plot indicating how the acoustic energy detected will change with crack size and is an illustration of the method of the present invention. This curve reflects changes at only one frequency; however, the entire spectrum amplitude should change in a like manner, thus, it is possible to draw a family of frequency spectra curves whose magnitude will change in the same fashion with regard to crack size. The saturated or choke flow curve is called Part 2 and indicates how acoustic energy increses with crack size. Before choke flow is reached, the flow is subsonic; thus from the time of crack initiation to choke flow the signal increases as the velocity to the 8th power and of course the diameter squared; viz, $kV^8d^2$. This is a relatively rapid variation because of the high exponent of velocity and will over power the diameter dependence. After choke flow occurs the variation or enlargement of the crack area is a proportional function; viz $kd^2$. Here the signal changes more slowly but is only a function of crack size. Thus, by either visual examination or use of computer 27 as shown in FIG. 2, by monitoring the change of the acoustic energy over time crack enlargement may be determined.

Yet another possible technique is illustrated by the curves of FIG. 4 where the choke flow condition is unique because of the saturation effect. Computer 27 of FIG. 2 could have stored in it a simulated pattern of this choke flow condition in a particular reactor and thus could recognize by the comparison such choke flow condition. And then by the monitoring in time of crack enlargement curves which vary as $kd^2$ crack diameter, d, could easily be determined. If a certain criteria was exceeded, the computer 27 would then generate an alarm.

Thus the present invention has provided an improved method of leak detection and monitoring.

What is claimed is:

1. A method of detecting and monitoring a leak caused by a through wall crack having a throat diameter in a high pressure fluid system comprising the following sequential steps: sensing the acoustic energy emitted by said wall crack, monitoring the change of said sensed energy over time, ascertaining that a choke flow condition exists wherein the escaping fluid velocity through said throat of said crack is sonic thus rendering the acoustic energy equal to a constant, $k\rho_o A^3_o$, multiplied by the square of the crack throat diameter, determining any crack enlargement in accordance with said change of said sensed energy.

* * * * *